United States Patent
Watanabe et al.

(10) Patent No.: US 6,346,621 B1
(45) Date of Patent: Feb. 12, 2002

(54) NITROGEN-HETEROCYCLIC COMPOUND AND PROCESS FOR PRODUCTION THEREOF

(75) Inventors: Makoto Watanabe; Toshihide Yamamoto; Masakazu Nishiyama, all of Yokkaichi (JP)

(73) Assignee: Tosoh Corporation, Yamaguchi (JP)

( * ) Notice: Subject to any disclaimer, the term of this patent is extended or adjusted under 35 U.S.C. 154(b) by 0 days.

(21) Appl. No.: 09/523,292

(22) Filed: Mar. 10, 2000

(30) Foreign Application Priority Data

| Mar. 10, 1999 | (JP) | 11-063692 |
| Mar. 10, 1999 | (JP) | 11-063693 |
| Mar. 10, 1999 | (JP) | 11-063694 |

(51) Int. Cl.[7] ............... C07D 241/02; C07D 209/20; C07D 215/58; C07D 401/02

(52) U.S. Cl. ............. 544/336; 546/135; 546/277.6; 548/336; 548/452; 548/467

(58) Field of Search ............. 544/336; 546/135, 546/277.4; 548/336, 452, 467

(56) References Cited

U.S. PATENT DOCUMENTS

| 4,707,553 A | 11/1987 | Satomura | 546/273 |
| 5,039,811 A | 8/1991 | Effland et al. | 546/273 |
| 5,776,955 A | 7/1998 | Huger et al. | 546/273 |

FOREIGN PATENT DOCUMENTS

| EP | 0287982 A2 | 10/1988 |
| EP | 0802173 A1 | 10/1997 |

OTHER PUBLICATIONS

Holger et al, "Reactions with monohydrazones of dicarbonyl . . . " Chem. Ber. vol. 111 No. 3, 1978, pp. 1195–1209.

Petrov et al, "Preparation and cyclization of 1–pentafluorophenyl . . . " Chem. Abs vol. 73 No. 5, Aug. 1970 Abs No. 25229.

Houlihan, "Indoles Part two" Wiley–Interscience pp. 191–192.

Houlihan, "Indoles Part two" Wiley–Interscience 1972, p. 270.

*Primary Examiner*—Richard L. Raymond
*Assistant Examiner*—Venkalaraman Balasubramanian
(74) *Attorney, Agent, or Firm*—Nixon & Vanderhye

(57) ABSTRACT

A nitrogen-heterocyclic compound is provided which is represented by General Formula (1):

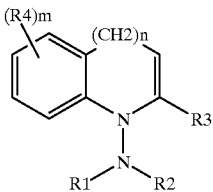

(1)

where $R^1$ and $R^2$ are independently hydrogen, an alkyl group, an aryl group, or a heteroaryl group; $R^3$ is hydrogen or an aryl group; $R^4$ is a substituted amino group, an alkoxy group, a nitro group, or halogen; m is an integer from 0 to 2; and n is 0 or 1. A process for producing the above compound is also provided. This compound is useful as a source material of medicines, pesticides, electronic materials, and intermediates for other substituted nitrogen-heterocyclic compounds.

20 Claims, No Drawings

NITROGEN-HETEROCYCLIC COMPOUND AND PROCESS FOR PRODUCTION THEREOF

BACKGROUND OF THE INVENTION

1. Field of the Invention

The present invention relates to nitrogen-heterocyclic compounds (nitrogen-containing heterocyclic compounds), and a process for producing the compound. More specifically, the present invention relates to nitrogen-heterocyclic compounds substituted at 1-position by an amino group, including 1-aminoindole derivatives and 1-amino-4H quinoline derivatives, and intermediates therefore.

The present invention relates also to a process for producing a nitrogen-heterocyclic compound including indole derivatives and 4H-quinoline derivatives, the process comprising cyclizing intramolecularly a hydrazone derivative having a halogenated aryl group in the presence of a catalyst composed of a phosphine and a palladium compound.

The present invention relates further to a process for producing a substituted indole derivative, comprising cyclizing intramolecularly a hydrazone derivative having a halogenated aryl group in the presence of a catalyst composed of a phosphine and a palladium compound, an amine, and a base, and introducing simultaneously an amino group to the non-nitrogen aromatic ring (aromatic ring not containing nitrogen).

These nitrogen-heterocyclic compounds are useful as a source material for medicines and pesticides, and for electronic materials.

2. Description of the Related Art

Nitrogen-heterocyclic compounds substituted at 1-position by an amino group are disclosed: 1-(pyridylamino)-indoles are disclosed as an anancastic disease remedy in JP-A-7-53376 (the term "JP-A" herein means an "unexamined published Japanese patent application"), and 1-(phenylamino)indoles are disclosed in JP-A-60-142955.

On the other hand, many processes are investigated for the synthesis of nitrogen-heterocyclic compound. In particular, for indole derivatives, various processes are well known such as a Fischer process, a Reissert process, and a Bischler process. In recent years, new processes have been disclosed: a process starting from a nitrostyrene catalyzed by use of palladium-copper-oxygen disclosed in JP-A-3-24055; synthesis of an indole derivative by preparing an indoline compound in the presence of palladium/phosphine catalyst and dehydrogenating it in the presence of palladium carbon (S. L. Buchwald et al.: J. Am. Chem. Soc. 1998, Vol. 120, pp. 3068–3073); indole synthesis by catalytic cyclization of o-iodoaniline with a ketone in the presence of a palladium catalyst (C. Chen et al.: J. Org. Chem., 1997, Vol. 62, pp. 2676–2677); indole synthesis by catalytic cyclization of o-iodoaniline with an alkyne in the presence of a palladium catalyst (R. C. Larock et al: J. Org. Chem., 1998, Vol. 63, pp. 7652–7662); and indole synthesis by reductive cyclization employing an o-nitrotoluene derivative (A. D. Batcho et al.: Organic Syntheses, 1985, Vol. 63, pp.214–224).

A process for synthesis of 1-aminoindole is reported in which o-nitrosophenylethylamine is electrochemically converted (B. A. F. Uribe et al.: European Journal of Organic Chemistry, 1999, Vol.2, pp.419–430).

The arylpiperazine structure is important in remedy for brain malfunction such as an antidepressant. For example, arylpiperazines are useful for remedy for brain malfunction such as an antidepressant, and importance of this structure for pharmacological activity are described by R. A. Glennon et al.: Drug Development Research, 22 (1993), pp.25–36; R. M. Pindler et al.: Medicinal Research Reviews, 13 (1993), pp.259–325, and R. A. Glennon et al.: Journal of Medicinal Chemistry, 32 (1989), pp.1921–1926.

Diarylamines are described to be useful as the intermediates for medicines and pesticides and for electronic intermediate material in Yuki Gosei Kyokai-Shi (Journal of the Organic Synthesis Society, Japan), Vol.52 (1994) pp.1083–1088. Triarylamines having high electron carrying ability are described to be useful as a hole carrier in organic electroluminescence by Seizo MIYATA ("Organic EL Elements and Industrial Front Thereof", pp.22–27, pp.104–106, NTS Co.).

As shown above, the diarylamine or triarylamine structure having a longer conjugation system is superior to the monoarylamine structure in the properties and functions in the aforementioned application fields. The structure of diarylamine, triarylamine, or N-arylazole is essential to the electronic materials such as the hole carrier in organic electroluminescence.

However, in the aforementioned known nitrogen-heterocyclic compounds (namely, indole derivatives having an amino group at 1-position), the kinds of the substituents on the non-nitrogen aromatic ring are limited, and the position of the substitution is limited to 3- and 5-positions of the indole. The nitrogen-heterocyclic compound is not known which has an amino group at 1-position and has a non-nitrogen aromatic ring substituted by a 1-piperazinyl, arylamino, diarylamino, or azolyl group (the azolyl group including cyclic amino groups such as pyrrolyl and indolyl).

In the conventional production processes mentioned above, the source materials cannot readily be available, and in synthesis of substituted indole, the position of the substituent on the indole ring is limited mainly to 5-, 6-, or 7-position. For example, an indole derivative having a substituent at 4-position only cannot readily be synthesized by the conventional process.

The present invention has been made to solve the above problems of the prior art.

SUMMARY OF THE INVENTION

The present invention intend to provide a heterocyclic compound having, on the non-nitrogen aromatic ring, a substituent such as 1-piperazinyl, arylamino-, diarylamino, azolyl, alkoxy, and nitro.

The present invention intends also to provide a nitrogen-heterocyclic compound having a halogen atom on the aromatic ring useful as the source material of the above substituted nitrogen-heterocyclic compound.

The present invention intends further to provide a process for synthesizing, in a simple manner, the nitrogen-heterocyclic compound such as indole derivatives and 4H-quinoline derivatives useful as a source material for medicines, pesticides, and electronic materials from readily available source materials.

After comprehensive investigation to solve the above problems, the inventors of the present invention have found the nitrogen-heterocyclic compound of the present invention, and the process for production thereof. Thus the present invention has been completed.

In an aspect of the present invention, there is provided a nitrogen-heterocyclic compound represented by General Formula (1) below:

(1)

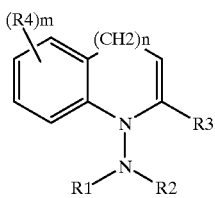

where $R^1$ and $R^2$ are independently hydrogen, an alkyl group, an aryl group, or a heteroaryl group; $R^3$ is hydrogen or an aryl group; $R^4$ is a substituted amino group, an alkoxy group, a nitro group, or halogen; m is an integer from 0 to 2; and n is 0 or 1. A process for producing the above compound is also provided.

In another aspect of the present invention, there is provided a nitrogen-heterocyclic compound represented by General Formula (2) below:

(2)

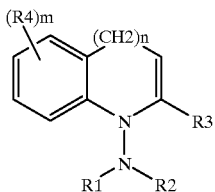

where $R^1$ and $R^2$ are independently hydrogen, an alkyl group, a phenyl group, a substituted phenyl group, a furyl group, or a thienyl group; $R^3$ is hydrogen or an aryl group; $R^4$ is a substituted amino group; m is 1 or 2; and n is 0 or 1. An intermediate thereof, and a process for producing the above compound are also provided.

In a further aspect of the present invention, there is provided a process for producing a substituted indole derivative represented by General Formula (7) below:

(7)

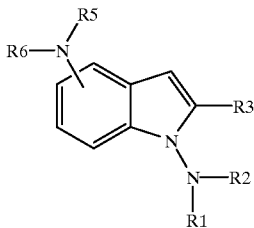

where $R^1$ and $R^2$ are independently hydrogen, an alkyl group, an aryl group, or a heteroaryl group; $R^3$ is hydrogen or an aryl group; $R^5$ and $R^6$ are independently hydrogen, an alkyl group, or an aryl group, and $R^5$ and $R^6$ may be linked suitably to form a hetero-ring.

DETAILED DESCRIPTION OF THE PREFERRED EMBODIMENTS

The present invention is described below in detail.
1. Nitrogen-Heterocyclic Compound Represented by General Formula (1):

In this embodiment of the present invention, the compound represented by General Formula (1) is produced by intramolecular cyclization of a hydrazone compound represented by General Formula (4) below having a halogenated aryl group in the presence of a catalyst containing a phosphine and a palladium compound, and a base:

(4)

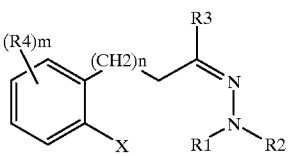

where $R^1$ and $R^2$ are independently hydrogen, an alkyl group, an aryl group, or a heteroaryl group; $R^3$ is hydrogen or an aryl group; $R^4$ is a substituted amino group, an alkoxy group, a nitro group, or halogen; X is a halogen; m is an integer from 0 to 2; and n is 0 or 1.

As the substitutents $R^1$ and $R^2$ in the hydrazone compound represented by General Formula (4) in the present invention, the alkyl group includes methyl, ethyl, propyl, butyl, and other lower alkyl groups; the aryl group includes phenyl, 4-tolyl, 4-trifluoromethylphenyl, and 4-methoxyphenyl; and the heteroaryl group includes 4-pyridyl, 3-pyridyl, 2-pyridyl, 2-furyl, and 2-thienyl. As the substituent $R^3$, the aryl group includes phenyl, 4-tolyl, 4-trifluoromethylphenyl, 4-methoxyphenyl, and 4-biphenyl. As the substituent $R^4$, the substituted amino group includes 1-piperazinyl, 4-methyl-1-piperazinyl, 3-methyl-1-piperazinyl, 1-homopiperazinyl, N-phenyl-N-methylamino, diphenylamino, di(p-tolyl)amino, N-(1-naphthyl)-N-phenylamino, N-(2-naphthyl)-N-phenylamino, N-(2-fluorenyl)-N-phenylamino, 1-pyrrolyl, 1-indolyl, and 9-carbazolyl; the alkoxy group includes methoxy, ethoxy, butoxy, 4,5-methylenedioxy, and 5,6-methylenedioxy; and the halogen includes fluorine, chlorine, bromine, and iodine. The halogen X includes chlorine, bromine, and iodine.

The method of synthesis of the hydrazone compound represented by General Formula (4) is described below.

The hydrazone compound represented by General Formula (4) in which n is 0 can be synthesized, for example, through the steps shown by formulas below:

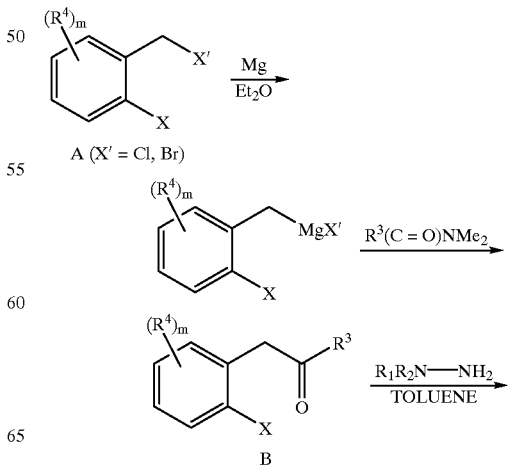

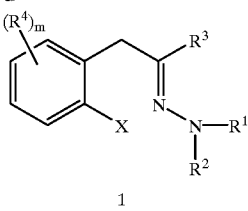

As shown above, a benzyl halide (A) having a halogen X at 2-position and a substituent $R^4$ is brought into contact with magnesium in ether to form a corresponding benzyl Grignard reagent. This benzyl Grignard reagent is allowed to react with N,N-dimethyl carboxylic acid amide ($R^3CONMe_2$). The product (B), a benzyl ketone or a benzyl aldehyde ($R^3$=H), is allowed to react with a hydrazine ($R^1R^2NNH_2$) in toluene to obtain a hydrazone derivative (1) (General Formula (4) in which n is 0) which is the source substance of the process of this embodiment. Various halogen-substituted benzyl halides (A) such as 2-chlorobenzyl chloride, 2,6-dichlorobenzyl chloride, 2,4-dichlorobenzyl chloride, and 2,5-dichlorobenzyl chloride are commercially readily available. 2-Chlorotoluene, methoxy-2-bromotoluene, dichlorotoluenes, and nitro-2-chlorotoluene are also readily available, and the methyl group thereof can be chlorinated or brominated by a conventional method to obtain the halogen-substituted benzyl halide. In such a manner, the source substance hydrazone for this embodiment can be synthesized from a readily available compound. In this synthesis, the yield of the hydrazone derivative ranges from 50% to 60% based on the halogenated benzyl halide (A).

The hydrazone compound represented by General Formula (4) in which n is 1 can be synthesized, for example, through the steps shown by formulas below:

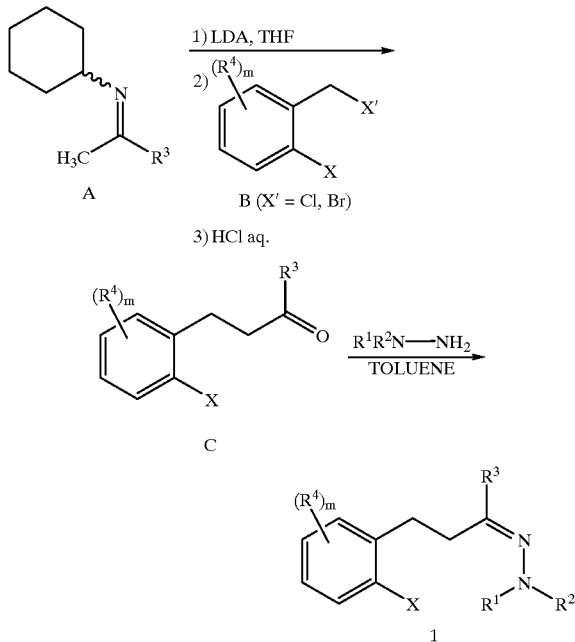

As shown above, a lithium enamide prepared from lithium diisopropylamide (LDA) and an N-cyclohexylimine (A) of acetaldehyde or an arylmethyl ketone, and a benzyl halide (B) having X at 2-position and a substituent $R^4$ on the benzene ring are allowed to react in THF to obtain a carbonyl compound (C) having the corresponding substituents. The N-cyclohexylimine (A) and the corresponding lithium enamide can be prepared according to the known method (described in Organic Syntheses, Collective Volume VI, 1988, pp.901–904). The resulting compound (C) is allowed to react with a hydrazine ($R^1R^2NNH_2$) in toluene to synthesize the hydrazone derivative (1) (General Formula (4) in which n is 1) which is a source substance of the process of this embodiment. In this synthesis, the yield of the hydrazone derivative is in the range from 50% to 70% based on the halogen-substituted benzyl halide (B).

In the above reactions, a catalyst comprising a palladium compound and a phosphine is added to the reaction system. The catalyst components may be separately added to the reaction system, or may be added thereto as a preliminarily formed complex.

The palladium compound used in this embodiment is not specially limited, and includes
  divalent palladium compounds such as palladium(II) chloride, palladium(II) bromide, palladium(II) acetate, palladium (II) acetylacetonate, dichlorobis(benzonitrile)palladium(II), dichlorobis(acetonitrile) palladium(II), dichlorobis(triphenylphosphine) palladium(II), dichlorotetraammine palladium(II), dichloro(cycloocta-1,5-diene)palladium(II), and palladium (II) trifluoroacetate; and zero-valent palladium compounds such as tris(dibenzylideneacetone) dipalladium(0), tris(dibenzylideneacetone) dipalladium (0) chloroform complex, and tetrakis (triphenylphosphine)palladium(0).

Of these, particularly preferred are palladium acetate, and tris(dibenzylideneacetone)dipalladium(0). The amount of the palladium compound used for the reaction is not specially limited, but ranges preferably from 0.001 to 10 mole %, more preferably from 0.005 to 7 mole %, still more preferably from 0.005 to 5 mole % in terms of palladium based on the compound represented by General Formula (4).

The phosphine used in this embodiment includes
  specifically phosphines having a t-butyl/phosphorus linkage such as tri-t-butylphosphine, 1-(N,N-dimethylaminomethyl)-2-(di-t-butylphosphino)-ferrocene, 1-(methoxymethyl)-2-(di-t-butylphosphino) ferrocene, 1,1'-bis(di-t-butylphosphino)ferrocene, 2,2'-bis(di-t-butylphosphino)-1,1'-binaphthyl, 2-methoxy-2'-(di-t-butylphosphino)-1,1'-binaphthyl, 2-(di-t-butylphosphino)biphenyl, 2-(di-t-butylphosphino)-2'-dimethylaminobiphenyl, 2-(di-t-butylphosphino)-2'-dimethylamino-1,1'-binaphthyl, (di-t-butylphosphino) ferrocene, and 9,9-dimethyl-4,5-bis(di-t-butylphosphino)xanthene;

aromatic phosphines such as tri(o-tolyl)phosphine, 2,2'-bis(diphenylphosphino)-1,1'-binaphthyl, 1-(N,N-dimethylaminomethyl)-2-(diphenylphosphino)ferrocene, and 1-(methoxymethyl)-2-(diphenylphosphino)ferrocene; and 9,9-dimethyl-4,5-bis(diphenylphosphino)xanthene.

Of these, preferred are the phosphines having a t-butyl/phosphorus linkage which is capable of improving remarkably the activity and selectivity of the reaction. The amount of the phosphine to be added to the reaction system is not specially limited, but ranges preferably from 0.5 to 10 moles, more preferably from 0.8 to 5 moles, per mole of the palladium compound.

The base used in this embodiment is not limited, and may be selected from organic bases and inorganic bases. The preferred base includes specifically sodium hydride, potassium hydride, lithium hydride, sodium amide, potassium amide, lithium amide, potassium carbonate, sodium carbonate, lithium carbonate, rubidium carbonate, cesium carbonate, potassium hydrogencarbonate, sodium hydrogencarbonate, sodium metal, potassium metal, lithium metal, methoxysodium, methoxypotassium, ethoxysodium, ethoxypotassium, ethoxylithium, t-butoxylithium, t-butoxysodium, and t-butoxypotassium. Of these bases, particularly preferred are t-butoxysodium, and carbonates. The amount of the base to be added to the reaction system is preferably in the range from 0.7 to 3.2 moles, more preferably from 0.9 to 2.4 moles, per mole of the compound represented by General Formula (4).

The above reaction is conducted usually in an inert solvent. The solvent is not limited, provided that the reaction is not significantly retarded. The solvent includes, aromatic hydrocarbon solvents such as benzene, toluene, and xylene; ether solvents such as diethyl ether, tetrahydrofuran, and dioxane; acetonitrile; dimethylformamide; dimethylsulfoxide; and hexamethylphosphoric triamide. Particularly preferred are aromatic hydrocarbons including benzene, toluene, and xylene.

The above reaction is conducted usually at an ordinary pressure in an inert gas atmosphere of nitrogen, argon, or the like, but may be conducted under pressure. The reaction temperature ranges preferably from 20 to 300° C., more preferably from 50 to 200° C. The reaction time ranges from several minutes to 72 hours, depending on the reaction conditions, the compound represented by General Formula (4), the palladium compound, and so forth. After the reaction, the intended compound can be obtained by treating the reaction mixture by a conventional manner.

The compound represented by General Formula (1) which can be produced in this embodiment includes indole derivatives such as 1-(dimethylamino)indole, 1-(methylamino)indole, 1-(ethylamino)indole, 1-(phenylamino)indole, 1-(diphenylamino)indole, 1-(N-phenyl-N-methylamino)indole, 1-[(N-(4-pyridyl)-N-methylamino]indole, 1-[(N-(3-pyridyl)-N-methylamino]indole, 1-[(N-(2-pyridyl)-N-methylamino]indole, 1-[(N-(2-furyl)-N-methylamino] indole, 1-[(N-(2-thienyl)-N-methylamino]indole, 1-[(N-(4-trifluoromethylphenyl)-N-methylamino] indole, 1-[((N-(4-tolyl)-N-methylamino]indole, 1-[(N-(4-methoxyphenyl)-N-methylamino]indole, 1-(dimethylamino)-2-phenylindole, 1-(dimethylamino)-4-chloroindole, 1-(diphenylamino)-4-chloroindole, 1-(dimethylamino)-4-chloro-2-phenylindole, 1-(dimethylamino)-5-choroindole, 1-(dimethylamino)-6-chloroindole, 1-(dimethylamino)-7-chloroindole, 1-(dimethylamino)-4-fluoroindole, 1-(dimethylamino)-4-bromoindole, 1-(N-phenyl-N-methylamino)-5-chloroindole, 1-(dimethylamino)-4-methoxyindole, 1-(dimethylamino)-4-butoxyindole, 1-(dimethylamino)-4-nitroindole, 1-(dimethylamino)-4,5-methylenedioxyindole, 1-(dimethylamino)-5,6-methylenedioxyindole, 4-(1-piperazinyl)-1-(dimethylamino)indole, 4-(1-piperazinyl)-1-(diphenylamino)indole, 4-(1-piperazinyl)-1-(N-phenyl-N-methylamino)indole, 4-(1-piperazinyl)-1-[(N-(2-furyl)-N-methylamino]indole, 4-(1-piperazinyl)-1-[(N-(2-thienyl)-N-methylamino]indole, 4-(1-piperazinyl)-1-[(N-(4-trifluoromethylphenyl)-N-methylamino]indole, 4-(1-piperazinyl)-1-(dimethylamino)-2-phenylindole, 4-(N-phenyl-N-methylamino)-1-(dimethylamino)indole, 4-(N-phenyl-N-methylamino)-1-(diphenylamino)indole, 4-(diphenylamino)-1-(diphenylamino)indole, 4-[N-(1-naphthyl)-N-phenylamino]-1-(diphenylamino)indole, 4-(1-pyrrolyl)-1-(dimethylamino)indole, 6-(1-pyrrolyl)-1-(dimethylamino)indole, 4-(1-indolyl)-1-(dimethylamino)indole, 6-(1-piperazinyl)-1-(dimethylamino)indole, 4-(1-homopiperazinyl)-1-(dimethylamino)indole, 4-(3-methyl-1-piperazinyl)-1-(dimethylamino)indole, 4-di(p-tolyl)amino-1-(dimethylamino)indole, 6-(9-carbazolyl)-1-(dimethylamino)indole, 4,6-bis(diphenylamino)-1-(dimethylamino)indole, 7-(1-piperazinyl)-1-(dimethylamino)indole, 7-(dimethylamino)-1-(dimethylamino)indole, and 6-fluoro-1-(dimethylamino)indole: and 4H-quinoline derivatives such as 1-(dimethylamino)-4H-quinoline, 1-(methylamino)-4H-quinoline, 1-(N-phenyl-N-methylamino)-4H-quinoline, 1-[(N-(4-pyridyl)-N-methylamino]-4H-quinoline, 1-[(N-(3-pyridyl)-N-methylamino]-4H-quinoline, 1-(dimethylamino)-5-chloro-4H-quinoline, 1-(dimethylamino)-5-nitro-4H-quinoline, 1-(dimethylamino)-5-chloro-2-phenyl-4H-quinoline, 1-(dimethylamino)-7-chloro-4H-quinoline, 1-(dimethylamino)-6-chloro-4H-quinoline, 1-(dimethylamino)-6,7-methylenedioxy-4H-quinoline, 1-(dimethylamino)-5-(1-pyrrolyl)-4H-quinoline, 1-(dimethylamino)-5-(9-carbazolyl)-2-phenyl-4H-quinoline, 1-(dimethylamino)-7-(1-piperizinyl)-4H-quinoline, 1-(dimethylamino)-6-(1-piperizinyl)-4H-quinoline, 1-(dimethylamino)-5-(1-piperizinyl)-4H-quinoline, 1-(dimethylamino)-5-(diphenylamino)-4H-quinoline, 1-(dimethylamino)-5,7-bis(diphenylamino)-2-phenyl-4H-quinoline, 5-fluoro-1-(dimethylamino)-4H-quinoline, and 8-(1-piperazinyl)-1-(dimethylamino)-4H-quinoline.

2. Nitrogen-Heterocyclic Compound Represented by General Formula (2), Intermediate Thereof, and Process for Production Thereof:

In the nitrogen-heterocyclic compound represented by General Formula (2) shown above or the halogenated nitrogen-heterocyclic compound represented by General Formula (3) below:

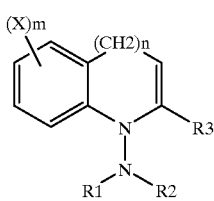

(3)

the substituents $R^1$ and $R^2$ are, in the present invention, independently hydrogen, an alkyl group, a phenyl group, a substituted phenyl group, a furyl group, or a thienyl group. The alkyl group includes methyl, ethyl, propyl, and butyl. The substituted phenyl includes 4-tolyl, 4-(t-butyl)phenyl, 4-fluorophenyl, 3-trifluoromethylphenyl, and 4-methoxyphenyl.

In the nitrogen-heterocyclic compound represented by General Formula (2) shown above or the halogenated nitrogen-heterocyclic compound represented by General Formula (3) above, in the present invention, the substituent $R_3$ is hydrogen, or an aryl group. The aryl group includes specifically phenyl, 4-tolyl, 4-fluorophenyl, 3-trifluoromethylphenyl, 4-methoxyphenyl, and 4-biphenyl.

In the nitrogen-heterocyclic compound represented by General Formula (2), the substituent $R^4$ is a substituted amino group. The amino group includes specifically 1-piperazinyl, 4-methyl-piperazinyl, 3-methyl-1-piperazinyl, 1-homopiperazinyl, N-phenyl-N-methyl, diphenylamino, di(p-tolyl)amino, N-(1-naphthyl)-N-phenylamino, N-(2-naphthyl)-N-phenylamino, N-(2-fluorenyl)-N-phenylamino, 1-pyrrolyl, 1-indolyl, and 9-carbazolyl.

In the halogenated nitrogen-heterocyclic compound represented by General Formula (3), the substituent X is a halogen. The halogen specifically includes fluorine, chlorine, bromine, and iodine.

The nitrogen-heterocyclic compound represented by General Formula (2) in the present invention specifically includes indole derivatives such as 4-(1-piperazinyl)-1-(dimethylamino)indole, 4-(1-piperazinyl)-1-(diphenylamino)indole, 4-(1-piperazinyl)-1-(N-phenyl-N-methylamino)indole, 4-(1-piperazinyl)-1-[(N-(2-furyl)-N-methylamino]indole, 4-(1-piperazinyl)-1-[(N-(2-thienyl)-N-methylamino]indole, 4-(1-piperazinyl)-1-[(N-(4-trifluoromethylphenyl)-N-methylamino]indole, 4-(1-piperazinyl)-1-(dimethylamino)-2-phenylindole, 4-(N-phenyl-N-methylamino)-1-(dimethylamino)indole, 4-(N-phenyl-N-methylamino)-1-(diphenylamino)indole, 4-(N-diphenylamino)-1-(diphenylamino)indole, 4-[N-(1-naphthyl)-N-phenylamino]-1-(diphenylamino)indole, 4-(1-pyrrolyl)-1-(dimethylamino)indole, 6-(1-pyrrolyl)-1-(dimethylamino)indole, 4-(1-indolyl)-1-(dimethylamino)indole, 6-(1-piperazinyl)-1-(dimethylamino)indole, 7-(1-piperazinyl)-1-(dimetylamino)indole, 6-(1-pyrrolyl)-1-(dimethylamino)indole, 4-(1-homopiperizinyl)-1-(dimethylamino)indole, 4-(3-methyl-1-piperazinyl)-1-(dimethylamino)indole, 4-di(p-tolyl)amino-1-(dimethylamino)indole, 6-(9-carbazolyl)-1-(dimethylamino)indole, and 4,6-bis(diphenylamino)-1-(dimethylamino)indole; and 4H-quinoline derivatives such as 1-(dimethylamino)-5-(1-pyrrolyl)-4H-quinoline, 1-(dimethylamino)-5-(9-carbazolyl)-2-phenyl-4H-quinoline, 1-(dimethylamino)-7-(1-piperazinyl)-4H-quinoline, 1-(dimethylamino)-6-(1-piperazinyl)-4H-quinoline, 1-(dimethylamino)-5-(1-piperazinyl)-4H-quinoline, 1-(dimethylamino)-5-(diphenylamino)-4H-quinoline, and 1-(dimethylamino)-5,7-bis(diphenylamino)-2-phenyl-4H-quinoline.

The halogenated nitrogen-heterocyclic compound represented by General Formula (3) includes specifically indole derivatives such as 4-chloro-1-(dimethylamino)indole, 4-chloro-1-(diphenylamino)indole, 4-chloro-1-(N-phenyl-N-methylamino)indole, 4-chloro-1-[N-(2-furyl)-N-methylamino]indole, 4-chloro-1-[N-(2-thienyl)-N-methylamino]indole, 4-chloro-1-[N-(4-trifluoromethylphenyl)-N-methylamino]indole, 4-chloro-1-(dimethylamino)-2-phenylindole, 4-bromo-1-(dimethylamino)indole, 4-iodo-1-(dimethylamino)indole, 4-fluoro-1-(diphenylamino)indole, 6-chloro-1-(diphenylamino)indole, 5-chloro-1-(dimethylamino)indole, 6-bromo-1-(dimethylamino)indole, 7-chloro-1-(dimethylamino)indole, 4,6-dichloro-1-(dimethylamino)indole, 4,6-dibromo-1-(dimethylamino)indole, 4-fluoro-1-(dimethylamino)indole, and 6-fluoro-4-fluoro-1-(dimethylamino)indole; and 4H-quinoline derivatives such as 1-(dimethylamino)-5-chloro-4H-quinoline, 1-(dimethylamino)-5-chloro-2-phenyl-4H-quinoline, 1-(dimethylamino)-7-chloro-4H-quinoline, 1-(dimethylamino)-6-chloro-4H-quinoline, 1-(dimethylamino)-5-bromo-4H-quinoline, 1-(dimethylamino)-5-iodo-4H-quinoline, 1-(dimethylamino)-5,7-dichloro-2-phenyl-4H-quinoline, 5-fluoro-1-(dimethylamino)-4H-quinoline, and 7-fluoro-1-(dimethylamino)-4H-quinoline.

The processes for producing the nitrogen-heterocyclic compound represented by General Formula (2), and for producing the halogenated nitrogen-heterocyclic compound represented by General Formula (3) in the present invention are explained below. Naturally, the process for producing the nitrogen-heterocyclic compound represented by General Formula (2) and the halogenated nitrogen-heterocyclic compound represented by General Formula (3) of the present invention is not limited to that described below.

The halogenated nitrogen-heterocyclic compound represented by General Formula (3) can be synthesized, for example, by the steps shown below. A hydrazone derivative represented by General Formula (8) is cyclized intramolecularly in the presence of a catalyst comprising a phosphine and a palladium compound, and a base:

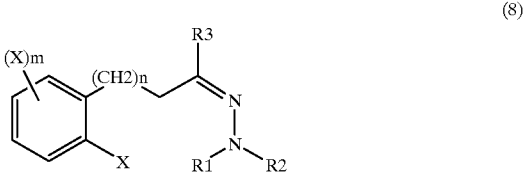

(8)

where $R^1$ and $R^2$ are independently hydrogen, an alkyl group, a phenyl group, a substituted phenyl group, a furyl group, or a thienyl group; $R^3$ is hydrogen or an aryl group; X is a halogen; m is 1 or 2; and n is 0 or 1.

In this reaction, a palladium compound and a phosphine are added in combination as the catalyst into the reaction system. The catalyst components may be separately added to the reaction system, or may be added thereto as a preliminarily formed complex.

The palladium compound includes palladium(II) chloride, palladium(II) bromide, palladium(II) acetate, tris(dibenzylideneacetone)dipalladium(0), tris(dibenzylideneacetone)dipalladium(0) chloroform complex, and tetrakis(triphenylphosphine)palladium(0). The amount of the palladium compound used for the reaction ranges preferably from 0.001 to 10 mole %, more preferably from 0.005 to 7 mole %, still more preferably from 0.005 to 5 mole % in terms of palladium based on the compound represented by General Formula (2).

The phosphine used in this embodiment includes specifically phosphines having a t-butyl/phosphorus linkage such as tri-t-butylphosphine, 1-(N,N-dimethylaminomethyl)-2-(di-t-butylphosphino)ferrocene, 1-(methoxymethyl)-2-(di-t-butylphosphino)ferrocene, 1,1'-bis(di-t-butylphosphino)ferrocene, 2,2'-bis(di-t-butylphosphino)-1,1'-binaphthyl, 2-methoxy-2-(di-t-butylphosphino)-1,1'-binaphthyl, 2-(di-t-butylphosphino)biphenyl, 2-(di-t-butylphosphino)-2'-dimethylaminobiphenyl, 2-(di-t-butylphosphino)-2'-dimethylamino-1,1'-binaphthyl, (di-t-butylphosphino)ferrocene, and 9,9-dimethyl-4,5-bis(di-t-butylphosphino)xanthene; aromatic phosphines such as tri(o-tolyl)phosphine, 2,2'-bis(diphenylphosphino)-1,1'-binaphthyl, 1-(N,N-dimethylaminomethyl)-2-(diphenylphosphino)ferrocene, and 1-(methoxymethyl)-2-(diphenylphosphino)ferrocene; and 9,9-dimethyl-4,5-bis(diphenylphosphino)xanthene.

Of these, preferred are the phosphines having a t-butyl/ phosphorus linkage which is capable of improving remarkably the activity and selectivity of the reaction. The amount of the phosphine to be added to the reaction system ranges preferably from 0.5 to 10 moles, more preferably from 0.8 to 5 moles, per mole of the palladium compound.

The base employed includes carbonates such as potassium carbonate, sodium carbonate, lithium carbonate, rubidium carbonate, and cesium carbonate; t-butoxylithium; t-butoxysodium; and t-butoxypotassium. The base is used in an amount ranging preferably from 0.7 to 3.2 moles, more preferably from 0.9 to 2.4 moles per mole of the compound represented by General Formula (8).

The above reaction is conducted usually in an inert solvent. The preferred solvent includes aromatic hydrocarbon solvents such as benzene, toluene, and xylene.

The above reaction is conducted under an ordinary pressure in an inert gas atmosphere of nitrogen, argon, or the like, but may be conducted under pressure. The reaction temperature is preferably in the range from 20 to 300° C., more preferably from 50 to 200° C. The reaction time is in the range from several minutes to 72 hours, depending on the reaction conditions, the compound represented by General Formula (3), the palladium compound, and so forth. After the reaction, the intended compound can be obtained by treating the reaction mixture by a conventional manner.

The hydrazone compound represented by General Formula (8), which is the source substance of the halogenated nitrogen-heterocyclic compound represented by General formula (3), can be synthesized, for example, through the steps shown below.

The hydrazone compound represented by General Formula (8) in which n is 0 can be synthesized, for example, through the steps shown below. A benzyl halide having a halogen X at 2-position and another halogen X on the benzene ring is brought into contact with magnesium in ether to form a corresponding benzyl Grignard reagent. This benzyl Grignard reagent is allowed to react with N,N-dimethyl carboxylic acid amide ($R^3CONMe_2$). The product (B), a benzyl ketone or a benzyl aldehyde ($R^3$=H), is allowed to react with a hydrazine ($R^1R^2NNH_2$) in toluene to obtain a hydrazone derivative of n=0 which is the source substance of the process of this embodiment. Various halogen-substituted benzyl halide such as 2,6-dichlorobenzyl chloride, 2,4-dichlorobenzyl chloride, and 2,5-dichlorobenzyl chloride are commercially readily available. Otherwise, a dichlorotoluene, which is readily available, can be chlorinated or brominated at the methyl group thereof by a conventional method to obtain the halogen-substituted benzyl halide. In such a manner, the hydrazone, the source material in this embodiment, can be synthesized from a readily available compound. In this synthesis, the yield of the hydrazone derivative ranges from 50% to 60% based on the halogenated benzyl halide.

The hydrazone compound represented by General Formula (8) in which n is 1 can be synthesized, for example, through the steps shown as below. A lithium enamide prepared from lithium diisopropylamide (LDA) and an N-cyclohexylimine of acetaldehyde or an arylmethyl ketone, and a benzyl halide having a halogen X at 2-position and another halogen X on the benzene ring are allowed to react in THF to obtain a carbonyl compound having the corresponding substituents. The N-cyclohexylimine and the corresponding lithium enamide can be prepared also according to the known method (described in Organic Syntheses, Collective Volume VI, 1988, pp.901–904). The resulting carbonyl compound is allowed to react with a hydrazine ($R^1R^2NNH_2$) in toluene to synthesize the hydrazone derivative of n=1 which is the source substance of the process of this embodiment. In this synthesis, the yield of the hydrazone derivative ranges from 50% to 70% based on the halogen-substituted benzyl halide (B).

On the other hand, the nitrogen-heterocyclic compound represented by General Formula (2) can be synthesized, for example, by reaction of a halogenated nitrogen-heterocyclic compound in the presence of an amine and a base with a catalyst composed of a phosphine and a palladium compound.

The amine includes piperazine, 1-methylpiperazine, 2-methylpiperazine, homopiperazine, N-phenyl-N-methylamine, diphenylamine, di(p-tolyl)amine, N-(1-naphthyl)-N-phenylamine, N-(2-naphthyl)-N-phenylamine, N-(2-fluorenyl)-N-phenylamine, pyrrole, indole, and carbazole.

The amine is used in an amount ranging usually from 0.7 to 6.0 moles, preferably from 0.7 to 3.2 moles per mole of the compound represented by General Formula (3). The catalyst, the base, and the reaction conditions are the same as in the synthesis of the nitrogen-heterocyclic compound in which $R^4$ is halogen.

3. Process for Producing Substituted Indole Represented by General Formula (7):

The compound represented by General formula (7) can be produced by intramolecular cyclization of a compound represented by General formula (5):

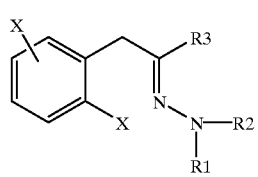

(5)

(where $R^1$ and $R^2$ are independently hydrogen, an alkyl group, an aryl group, or a heteroaryl group; $R^3$ is hydrogen or an aryl group; and X is a halogen), in the presence of a catalyst comprising a phosphine and a palladium compound, an amine represented by General Formula (6):

$R^5R^6NH$ (6)

(where $R^5$ and $R^6$ are independently hydrogen, an alkyl group, or an aryl group, and $R^5$ and $R^6$ may be linked to form a hetero-ring), and a base; and simultaneous introduction of an amino group onto the non-nitrogen aromatic ring.

In the hydrazone derivative represented by General Formula (5) in this embodiment, the alkyl group as the substituents $R^1$ and $R^2$ includes methyl, ethyl, propyl, and butyl; the aryl group as the substituents $R^1$ to $R^3$ includes phenyl, 4-tolyl, 4-trifluoromethylphenyl, 4-methoxyphenyl, and 4-biphenyl; the heteroaryl group as the substituents $R^1$ and $R^2$ includes 4-pyridyl, 3-pyridyl, 2-pyridyl, 2-furyl, and 2-thienyl; and the halogen X includes chlorine, bromine, and iodine.

The process for producing the hydrazone derivative represented by the above General Formula (5) having a halogenated aryl group is not specially limited. The hydrazone derivative, the source material of the production process of the present invention can be synthesized, for example, as below. A benzyl halide having a halogen X at 2-position and another halogen on the aromatic ring are brought into contact with magnesium in ether to form a corresponding benzyl Grignard reagent. This benzyl Grignard reagent is allowed to react with N,N-dimethyl carboxylic acid amide (R³CONMe₂). The product, a benzyl ketone or a benzyl aldehyde, is allowed to react with a hydrazine (R¹R²NNH₂) in toluene to obtain a hydrazone derivative which is the source substance of this embodiment. Various halogen-substituted benzyl halides such as 2,6-dichlorobenzyl chloride, 2,4-dichlorobenzyl chloride, and 2,5-dichlorobenzyl chloride are commercially available readily. Otherwise, dichlorotoluenes, which are readily available, can be chlorinated or brominated at the methyl group thereof by a conventional method to obtain the halogen-substituted benzyl halide. In such a manner, the hydrazone derivative, the source material in this embodiment, can be synthesized from readily available compounds. In this synthesis, the yield of the hydrazone derivative ranges from about 50% to about 60% based on the halogenated benzyl halide.

The amine represented by General Formula (6) in this embodiment includes specifically dimethylamine, diethylamine, di(n-butyl)amine, aniline, N-methylaniline, diphenylamine, di(p-tolyl)amine, di(p-methoxyphenyl) amine, di(p-fluorenyl)amine, di[m-(trifluoromethyl)phenyl] amine, m-(trifluormethyl)aniline, piperazine, 4-alkyl-1-piperazine, 3-methylpiperazine, homopiperazine, pyrrole, indole, and carbazole. The amine is used in an amount ranging preferably from 0.7 to 10 moles, more preferably from 0.9 to 6 moles per mole of the compound represented by the above General Formula (5).

In this reaction, a palladium compound and a phosphine are added in combination as the catalyst into the reaction system. The catalyst components may be separately added to the reaction system, or may be added thereto as a preliminarily formed complex.

The palladium compound used in this embodiment is not specially limited, and includes divalent palladium compounds such as palladium(II) chloride, palladium(II) bromide, palladium(II) acetate, palladium(II) acetylacetonate, dichlorobis(benzonitrile)palladium(II), dichlorobis(acetonitrile) palladium(II), dichlorobis(triphenylphosphine) palladium(II), dichlorotetraanmine palladium(II), dichloro(cycloocta-1,5-diene)palladium(II), and palladium(II) trifluoroacetate; and zero-valent palladium compounds such as tris (dibenzylideneacetone)dipalladium(0), tris (dibenzylideneacetone)dipalladium(0) chloroform complex, and tetrakis(triphenylphosphine)palladium (0).

Of these, particularly preferred are palladium acetate, and tris(dibenzylideneacetone)dipalladium(0). The amount of the palladium compound used for the reaction is not limited, and ranges preferably from 0.001 to 10 mole %, more preferably from 0.005 to 7 mole %, still more preferably from 0.005 to 5 mole % in terms of palladium based on the compound represented by General Formula (5).

The phosphine used in this embodiment includes specifically phosphines having a t-butyl-phosphorus linkage such as tri-t-butylphosphine, 1-(N,N-dimethylaminomethyl)-2-(di-t-butylphosphino)ferrocene, 1-(methoxymethyl)-2-(di-t-butylphosphino)ferrocene, 1,1'-bis(di-t-butylphosphino) ferrocene, 2,2'-bis(di-t-butylphosphino)-1,1'-binaphthyl, 2-methoxy-2'-(di-t-butylphosphino)-1,1'-binaphthyl, 2-(di-t-butylphosphino)biphenyl, 2-(di-t-butylphosphino)-2'-dimethylaminobiphenyl, 2-(di-t-butylphosphino)-2'-dimethylamino-1,1'-binaphthyl, (di-t-butylphosphino) ferrocene, and 9,9-dimethyl-4,5-bis(di-t-butylphosphino) xanthene;

aromatic phosphines such as tri(o-tolyl)phosphine, 2,2'-bis(diphenylphosphino)-1,1'-binaphthyl, 1-(N,N-dimethylaminomethyl)-2-(diphenylphosphino) ferrocene, and 1-(methoxymethyl)-2-(diphenylphosphino)ferrocene; and 9,9-dimethyl-4,5-bis(diphenylphosphino)xanthene.

Of these, preferred are the phosphines having a t-butyl-phosphorus linkage which is capable of improving remarkably the activity and selectivity of the reaction. The amount of the phosphine to be added to the reaction system is not specially limited, but is preferably in the range from 0.5 to 10 moles, more preferably from 0.8 to 5 moles, per mole of the palladium compound.

The base used in this embodiment is not limited, and may be selected from organic bases and inorganic bases. The preferred base includes specifically sodium hydride, potassium hydride, lithium hydride, sodium amide, potassium amide, lithium amide, potassium carbonate, sodium carbonate, lithium carbonate, rubidium carbonate, cesium carbonate, potassium hydrogencarbonate, sodium hydrogencarbonate, sodium metal, potassium metal, lithium metal, methoxysodium, methoxypotassium, ethoxysodium, ethoxypotassium, ethoxylithium, t-butoxylithium, t-butoxysodium, and t-butoxypotassium. Of these bases, particularly preferred are t-butoxysodium, and carbonates. The amount of the base to be added to the reaction system is preferably in the range from 0.7 to 5 moles, more preferably from 0.9 to 3 moles, per mole of the compound represented by General Formula (5).

The above reaction is conducted usually in an inert solvent. The solvent is not limited, provided that the reaction is not significantly retarded. The solvent includes, aromatic hydrocarbon solvents such as benzene, toluene, and xylene; ether solvents such as diethyl ether, tetrahydrofuran, and dioxane; acetonitrile; dimethylformamide; dimethylsulfoxide; and hexamethylphosphoric triamide. Particularly preferred are aromatic hydrocarbons including benzene, toluene, and xylene.

The above reaction is conducted usually under an ordinary pressure in an inert gas atmosphere of nitrogen, argon, or the like, but may be conducted under pressure. The reaction temperature ranges preferably from 20 to 300° C., more preferably from 50 to 200° C. The reaction time ranges from several minutes to 72 hours, depending on the reaction conditions, the compound represented by General Formula (5), the palladium compound, and so forth. After the reaction, the intended compound can be obtained by treating the reaction mixture by a conventional manner.

The substituted indole derivative represented by the above General Formula (7) produced according to the present invention includes specifically indole derivatives such as 4-dimethylamino-1-(dimethylamino)indole, 4-dibutylamino-1-(methylamino)indole, 4-(N-phenyl-N-methylamino)-1-(diphenylamino)indole, 4-(-piperazinyl)-1-(dimethylamino)indole, 4-(1-piperazinyl)-1-(diphenylamino)indole, 4-(1-piperazinyl)-1-(N-phenyl-N-methylamino)indole, 4-(1-piperazinyl)-1-[(N-(4-pyridyl)-N-methylamino]indole, 4-(1-piperazinyl)-1-[(N-(3-pyridyl)-N-methylamino]indole, 4-(1-piperazinyl)-1-[(N-(2-furyl)-N-methylamino] indole, 4-(1-piperazinyl)-1-[(N-(2-thienyl)-N-methylamino]indole, 4-(1-piperazinyl)-1-[(N-(4-trifluoromethylphenyl)-N-methylamino]indole, 4-(1-piperazinyl)-1-(dimethylamino)-2-phenylindole, 4-(1-pyrrolyl)-1-(dimethylamino)indole, 4-(1-indolyl)-1-(dimethylamino)indole, 6-(-piperazinyl-1-(dimethylamino)indole, 6-(1-pyrrolyl)-1-(dimethylamino)indole, 4-(1-homopiperazinyl)-1-

(dimethylamino)indole, 4-(3-methyl-1-piperazinyl)-1-(dimethylamino)indole, and 4-(9-carbazolyl)-1-(dimethylamino)indole.

(Effects of the Invention)

The nitrogen-heterocyclic compound of the present invention is a novel compound having a substituent additionally at 4-position of an indole ring, and are highly useful as the source substance for medicines and pesticides, and for electronic materials.

The present invention has made possible the synthesis of the useful nitrogen-heterocyclic compound from a readily available hydrazone derivative having a halogenated aryl group by intramolecular cyclization thereof in the presence of a catalyst composed of a palladium compound and a phosphine, and a base. The nitrogen-heterocyclic compounds including the indoles and the 4H-quinolines produced according to the present invention has a 1-amino structure in which the nitrogen of the amino group is directly bonded to the nitrogen of the ring. The compound having such a structure is disclosed as a useful compound for use for a medicine in JP-A-7-53376. However, it was extremely difficult to prepare the compound by a prior art technique. The present invention has made possible the easy synthesis of the compound. By prior art techniques, the introduction of a substituent selectively to 4-position of the indole ring requires considerable time and labor. The present invention has made possible this selective substituent introduction by use of readily available source substances.

On the other hand, the product of the present invention can readily be cleaved at the nitrogen-nitrogen bond by hydrogenation reduction, thereby enabling producing a nitrogen-heterocyclic compound having no substituent on the nitrogen. Further, the product of the present invention includes the one having a halogen on the benzene ring moiety. This halogen can be converted to an amino group, an aryl group, or a substituted vinyl group by use of the palladium-phosphine catalyst. Therefore, the compounds provided by the present invention are highly useful as the intermediate for nitrogen-heterocyclic compounds having various substituents.

Examples of the present invention are show below without limiting the invention in any way.

REFERENCE EXAMPLE 1

(Synthesis of 2,6-dichlorophenylacetaldehyde N,N-dimethylhydrazone)

A 200-mL three-necked flask equipped with a thermometer, a dropping funnel, a three-way stopcock, and a mechanical stirrer was purged with nitrogen. Thereto, were added 1.85 g (76 mmol) of magnesium, and 30 mL of diethyl ether. The dropping funnel was filled with a solution of 13.5 g (69 mmol) of 2,6-dichlorobenzyl chloride (produced by Tokyo Kasei K.K.) in 40 mL of diethyl ether. The solution was added dropwise into the flask by keeping the temperature of the reaction system at about 30° C. Thereafter, the reaction mixture was aged at room temperature for 30 minutes, and cooled with ice. Thereto, 6 g (82 mmol) of N,N-dimethylformamide was added dropwise. The reaction mixture was aged at room temperature for one hour, cooled with ice, and poured into 50 mL of 3N hydrochloric acid solution. The mixture was allowed to separate into phases, and the separated matter was extracted with diethyl ether. The combined organic phase was dried over anhydrous sodium sulfate. After filtration and concentration, 5 mL of methyl t-butyl ether was added to the concentration residue, and the mixture was heated to dissolve the residue. After cooling of the solution to room temperature, the deposited crystalline matter was collected by filtration to obtain 8.1 g (43 mmol) of crystalline 2,6-dichlorophenylacetaldehyde. (Yield: 62%)

A 1.0 g portion of Molecular Sieve 4A was placed in a 30-mL one-necked flask. The flask was purged with nitrogen. Into this flask, 1.01 g (5.3 mmol) of the above obtained 2,6-dichlorophenylacetaldehyde was put, and was dissolved by addition of 4 mL of toluene. With ice cooling, 351 mg (5.8 mmol) of N,N-dimethylhydrazine was added thereto. The mixture was stirred at room temperature for 3 hours. Thereafter, the reaction mixture was filtered, and the filtrate was concentrated. The concentration solution was distilled under a vacuum of 2 mmHg to obtain 1.14 g (4.9 mmol) of 2,6-dichlorophenylacetaldehyde N,N-dimethylhydrazone. (Yield: 93%).

REFERENCE EXAMPLE 2

2,4-Dichlorophenylacetaldehyde N,N-dimethylhydrazone was prepared in the same manner as in Reference Example 1 except that 2,4-dichlorobenzyl chloride (produced by Wako Pure Chemical Co.) was used in place of 2,6-dichlorobenzyl chloride. (Yield: 53% based on 2,4-dichlorobenzyl chloride).

REFERENCE EXAMPLE 3

2-Chlorophenylacetaldehyde N,N-dimethylhydrazone was prepared in the same manner as in Reference Example 1 except that 2-chlorobenzyl chloride (produced by Wako Pure Chemical Co.) was used in place of 2,6-dichlorobenzyl chloride. (Yield: 58% based on 2-chlorobenzyl chloride).

REFERENCE EXAMPLE 4

(Synthesis of 3-(2,6-dichlorophenyl)propionaldehyde N,N-dimethylhydrazone)

Acetaldehyde N-cyclohexylimine (N-ethylidenecyclohexylamine) was prepared in a yield 6.9 g (52.6 mmol) and was allowed to react with lithium diisopropylamide according to the method described in Organic Syntheses, Collective Volume VI, 1988, pp.901–904.

Separately, a 100-mL three-necked flask equipped with a thermometer, a dropping funnel, a three-way stopcock, and a magnetic stirrer was purged with nitrogen. Thereto, were added 10.2 g (52.2 mmol) of 2,6-dichlorobenzyl chloride (produced by Tokyo Kasei K.K.), and 25 mL of tetrahydrofuran. To this solution, the above obtained solution of the lithium salt compound was added dropwise by keeping the temperature of the reaction system in the range from 15 to 20° C. The reaction mixture was aged at room temperature for 2 hours, and the cooled with ice. Thereto 3N hydrochloric acid solution was added to stop the reaction. The mixture was extracted with ether. The organic phase was dried over anhydrous sodium sulfate, filtered, and concentrated. To the flask containing the concentration residue, 10 g of Molecular Sieve 4A was added and the flask was purged with nitrogen. The concentration residue was dissolved by addition of 10 mL of toluene, and was cooled with ice. Thereto, 3.45 g (57.4 mmol) of N,N-dimethylhydrazine was added. The mixture was stirred at room temperature for 3 hours, and filtered. The filtrate was concentrated under a reduced pressure. The obtained concentration residue was purified by silica gel chromatography (Solvent: hexane, ratio of hexane:ethyl acetate=20:1) to obtain 7.42 g (30.3 mmol) of 3-(2,6-dichlorophenyl)propionaldehyde N,N-dimethylhydrazone. (Yield: 58% based on 2,6-dichlorobenzyl chloride).

EXAMPLE 1

A 30-mL three-necked flask equipped with a thermometer, a three-way stopcock, and a magnetic stirrer was purged with nitrogen. Thereto, were added 31.5 mg of tris(dibenzylideneacetone)dipalladium(0) (produced by Strem Co.; 0.069 mmol as palladium, 3.0 mol % based on 2-chlorophenylacetaldehyde N,N-dimethylhydrazone, the source substance), 264 mg (2. 74 mmol) of t-butoxysodium, 5 mL of o-xylene, 40.1 mg (0.104 mmol) of 1-(N,N-dimethylaminomethyl)-2-(di-t-butylphosphino)ferrocene, and 450 mg (2.29 mmol) of 2-chlorophenylacetaldehyde N,N-dimethylhydrazone, in the named order. The mixture was heated to 110° C., and stirred at that temperature for 4 hours. The mixture was cooled to room temperature. Thereto, 10 mL of water was added. The mixture was extracted with diethyl ether. The extract solution was dried over anhydrous sodium sulfate, and was concentrated. The concentration residue was purified by alumina column chromatography (solvent; hexane:diethyl ether=50:1). Thereby, 275 mg (1.72 nmol) of the intended product, 1-(dimethylamino)indole. (Yield: 75%, GC purity 99%).

EXAMPLE 2

1-(Dimethylamino)indole was prepared in the same manner as in Example 1 except that 42.2 mg (0.21 mmol) of tri(t-butyl)phosphine was used in place of 1-(N,N-dimethylaminomethyl)-2-(di-t-butylphosphino)ferrocene, and the reaction was conducted at 120° C. for 20 hours. (Yield: 41%).

EXAMPLE 3

4-Chloro-1-(dimethylamino)indole was prepared in the same manner as in Example 1 except that 2,6-dichlorophenylacetaldehyde N,N-dimethylhydrazone was used in place of 2-chlorophenylacetaldehyde N,N-dimethylhydrozone, and the reaction was conducted at 120° C. for 120 hours. (Yield: 35%).

EXAMPLE 4

4-Chloro-1-(dimethylamino)indole was prepared in the same manner except that cesium carbonate was used in place of t-butoxysodium. (Yield: 33%).

EXAMPLE 5

6-Chloro-1-(dimethylamino)indole was prepared in the same manner as in Example 1 except that 2,4-dichlorophenylacetaldehyde N,N-dimethylhydrazone was used in place of 2-chlorophenylacetaldehyde N,N-dimethylhydrazone, and the reaction was conducted at 120° C. for 8 hours. (Yield: 2'%).

EXAMPLE 6

4-Chloro-1-(N-phenyl-N-methylamino)indole was prepared in the same manner as in Example 1 except that 2,6-dichlorophenylacetaldehyde N-phenyl-N-methylhydrazone was used in place of 2-chlorophenylacetaldehyde N,N-dimethylhydrazone, and the reaction was conducted at 120° C. for 8 hours. (Yield: 39%).

EXAMPLE 7

5-Chloro-1-(dimethylamino)-4H-quinoline was prepared in the same manner as in Example 1 except that 3-(2,6-dichlorophenyl)propionaldehyde N,N-dimethylhydrazone was used in place of 2-chlorophenylacetaldehyde N,N-dimethylhydrazone, cesium carbonate was used in place of t-butoxysodium, and the reaction was conducted at 120° C. for 8 hours. (Yield: 35%).

$^1$H NMR (400 MHz, CDCl$_3$, TMS): δ=2.67 (s, 6H), 2.85–2.94 (m, 2H), 3.02–3.08 (m, 2H), 7.19 (t, J=7.4 Hz, 1H), 7.31 (d, J=6.7 Hz, 1H), 7.63 (d, J=7.4 Hz, 1H).

$^{13}$C NMR (100 MHz, CDCl$_3$, TMS): δ=28.12, 28.50, 46.24, 46.84, 47.61, 120.03; 129.16, 130.74, 140.93, 145.80, 166.88

Table 1 shows the source substances and the products of Examples 1–7.

TABLE 1

| Example No. | Source Substance | Product |
|---|---|---|
| 1 & 2 | 2-chlorophenylacetaldehyde N,N-dimethylhydrazone | 1-(dimethylamino)indole |
| 3 & 4 | 2,6-dichlorophenylacetaldehyde N,N-dimethylhydrazone | 4-chloro-1-(dimethylamino)indole |

TABLE 1-continued

| Example No. | Source Substance | Product |
|---|---|---|
| 5 | (2,4-dichlorophenyl)acetaldehyde N-methyl-N-methylhydrazone | 6-chloro-1-(dimethylamino)indole |
| 6 | (2,6-dichlorophenyl)acetaldehyde N-methyl-N-phenylhydrazone | 4-chloro-1-(N-methyl-N-phenylamino)indole |
| 7 | 3-(2,6-dichlorophenyl)propanal N,N-dimethylhydrazone | 5-chloro-1-(dimethylamino)-1,2,3,4-tetrahydroquinoline |

EXAMPLE 8

A 30-mL three-necked flask equipped with a thermometer, a three-way stopcock, and a magnetic stirrer was purged with nitrogen. Thereto, were added 31.5 mg of tris (dibenzylideneacetone) dipalladium (0) (produced by Strem Co.; 0.069 mmol as palladium, 3.0 mmol % based on 2,6-dichlorophenylacetaldehhyde N,N-dimethylhydrazone, the source substance), 264 mg (2.74 mmol) of t-butoxysodium, 5 mL of o-xylene, 40.1 mg (0.104 mmol) of 1-(N,N-dimethylaminomethyl)-2-(di-t-butylphosphino) ferrocene, and 529 mg (2.29 mmol) of 2,6-dichlorophenylacetaldehyde N,N-dimethylhydrazone, in the named order. The mixture was heated to 120° C., and stirred at that temperature for 8 hours. The mixture was cooled to room temperature. Thereto, 10 mL of water was added. The mixture was extracted with diethyl ether. The extract solution was dried over anhydrous sodium sulfate, and was concentrated. The concentration residue was purified by alumina column chromatography (solvent; hexane:diethyl ether=80:1). Thereby, 156 mg (0.80 mmol) of the intended product, 4-chloro-1-(dimethylamino)indole was obtained. (Yield: 35%, GC purity: 99%).

$^1$H NMR (400 MHz, CDCl$_3$, TMS): δ=2.89 (s, 6H), 6.58 (d, J=3.4 Hz 1H), 7.05–7.18 (m, 2H), 7.43 (d, J=3.4 Hz, 1H), 7.45 (d, J=7.4 Hz, 1H).

$^{13}$C NMR (100 MHz, CDCl$_3$, TMS): δ=47.00, 47.48, 99.07, 108.55, 119.40, 121.83, 122.45, 123.99, 126.04, 135.82

EXAMPLE 9

4-(1-piperizinyl-1-dimethylamino)indole was prepared in the same manner as in Example 8 except that 4-chloro-1-(dimethylamino)indole synthesized in Example 8 was used in place of 2,6-dichlorophenylacetaldehyde N,N-dimethylhydrazone as the source substance, palladium was used in an amount of 1.0 mol % based on the source substance, piperazine in 4 equivalents to the source substance was added, and the solvent in the alumina column chromatography was changed to ethyl acetate:methanol (10:1 to 5:1). (Yield: 95%).

$^1$H NMR (400 MHz, CDCl$_3$, TMS): δ=1.75 (brs, NH), 2.88 (s, 6H), 3.09 (t, J=4.7 Hz, 4H), 3.19 (t, J=4.7 Hz, 4H), 6.48 (d, J=3.4 Hz, 1H), 6.57 (d, J=7.4 Hz, 1H), 7.13 (t, J=7.4 Hz, 1H), 7.23 (d, J=8.7 Hz, 1H), 7.33 (d, J=4.0 Hz, 1H).

$^{13}$C NMR (100 MHz, CDCl$_3$, TMS): δ=46.48, 47.32, 51.50, 52.15, 52.85, 53.40, 99.19, 104.64, 106.54, 118.72, 119.57, 122.42, 136.07, 146.05.

EXAMPLE 10

6-Fluoro-1-(dimethylamino)indole was prepared in the same manner as in Example 8 except that 2-chloro-4-fluorophenylacetaldehyde N,N-dimethylhydrazone was used in place of 2,6-dichlorophenylacetaldehyde N,N-dimethylhydrazone. (Yield: 74%).

$^1$H NMR (400 MHz, CDCl$_3$, TMS): δ=2.88 (s, 6H), 6.45 (d, J=3.3 Hz, 1H), 6.84 (dt, J=2.2 Hz, 8.4 Hz, 1H), 7.21 (dd, J=2.2 Hz, 9.8 Hz, 1H), 7.36 (d, J=3.6 Hz, 1H), 7.46 (dd, J=8.4 Hz, 5.1 Hz, 1H).

EXAMPLE 11

5,6-Methylenedioxy-1-(dimethylamino)indole was prepared in the same manner as in Example 8 except that 2-chloro-4,5-methylenedioxyphenylacetaldehyde N,N-dimethylhydrazone was used in place of 2,6-dichlorophenylacetaldehyde N,N-dimethylhydrazone. (Yield: 30%).

$^1$H NMR (400 MHz, CDCl$_3$, TMS): δ=2.87 (s, 6H), 5.92 (s, 2H), 6.35 (d, J=3.3 Hz, 1H), 6.94 (s, 1H), 7.02 (s, 1H), 7.26 (d, J=3.3 Hz, 1H).

Table 2 summarizes the source substances and the products in Examples 8–11.

TABLE 2

| Example No. | Source Substance | Product |
|---|---|---|
| 8 | 2,6-dichlorophenylacetaldehyde N,N-dimethylhydrazone | 4-chloro-1-(dimethylamino)indole |
| 9 | 4-chloro-1-(dimethylamino)indole | 4-(1-piperazinyl)-1-(dimethylamino)indole |
| 10 | 4-fluoro-2-chlorophenylacetaldehyde N,N-dimethylhydrazone | 6-fluoro-1-(dimethylamino)indole |
| 11 | methylenedioxy-chlorophenylacetaldehyde N,N-dimethylhydrazone | methylenedioxy-1-(dimethylamino)indole |

EXAMPLE 12

A 30-mL three-necked flask equipped with a thermometer, a three-way stopcock, and a magnetic stirrer was purged with nitrogen. Thereto, were added 521 mg (6.0 mmol) of piperazine, 21.2 mg of tris(dibenzylideneacetone)-dipalladium(0) (produced by Strem Co.; 0.046 mmol as palladium, 3.0 mol % based on 2,6-dichlorophenylacetaldehyde N,N-dimethylhydrazone, the source substance), 331 mg (3.44 mmol) of t-butoxysodium, 5 mL of o-xylene, 26.7 mg (0.069 mmol) of 1-(N,N-dimethylaminomethyl)-2-(di-t-butylphosphino) ferrocene, and 350 mg (1.51 mmol) of 2,6-dichlorophenylacetaldehyde N,N-dimethylhydrazone, in the named order. The mixture was heated to 120° C., and stirred at that temperature for 20 hours. The mixture was cooled to room temperature. Thereto, 10 mL of water was added. The mixture was extracted with diethyl ether. The extract solution was dried over anhydrous sodium sulfate, and was concentrated. The concentration residue was purified by alumina column chromatography (solvent; ethyl acetate:methanol=5:1). Thereby, 111 mg (0.45 mmol) of the intended product, 4-(1-piperazinyl)-1-(dimethylamino)indole was obtained. The same NMR spectrum as in Example 9 was obtained. (Yield: 30%).

EXAMPLE 13

4-(1-piperazinyl)-1-(N-phenyl-N-methylamino)indole was prepared in the same manner as in Example 12 except that 2,6-dichlorophenylacetaldehyde N-phenyl-N-methylhydrazone was used in place of 2,6-dichlorophenylacetaldehyde N,N-dimethylhydrazone. (Yield: 32%).

$^1$H NMR (400 MHz, CDCl$_3$, TMS): δ=2.88–2.95 (m, 4H), 3.04–3.10 (m, 4H), 3.20 (s, 3H), 6.84 (t, J=7.3 Hz, 1H), 7.00 (t, J=5.8 Hz, 1H), 7.03 (t, J=4.8 Hz, 1H), 7.14–7.28 (m, 7H).

EXAMPLE 14

4-(N-phenyl-N-methylamino)-1-(dimethylamino)indole was prepared in the same manner as in Example 12 except that N-methylaniline was used in place of piperazine. (Yield: 34%).

$^1$H NMR (400 MHz, CDCl$_3$, TMS): δ=2.91 (s, 6H), 3.41 (s, 3H), 6.10 (d, J=3.3 Hz, 1H), 6.77 (t, J=7.3 Hz, 1H), 6.81 (d, J=7.7 Hz, 2H), 6.91 (dd, J=7.3 Hz, 1.1 Hz, 1H), 7.15–7.22 (m, 3H), 7.27 (d, J=3.6 Hz, 1H), 7.38 (d, J=8.0 Hz, 1H).

EXAMPLE 15

6-(1-piperazinyl)-1-(dimethylamino)indole was prepared in the same manner as in Example 12 except that 2,4-dichlorophenylacetaldehyde N,N-dimethylhydrazone was used in place of 2,6-dichlorophenylacetaldehyde N,N-dimethylhydrazone. (Yield: 30%).

EXAMPLE 16

6-(1-pyrrolyl)-1-(dimethylamino)indole was prepared in the same manner as in Example 12 except that 2,4- dichlorophenylacetaldehyde N,N-dimethylhydrazone was used in place of 2,6-dichlorophenylacetaldehyde N,N-dimethylhydrazone, tri(t-butyl)phosphine was used in place of 1-(N,N-dimethylaminomethyl)-2-(di-t-butylphosphino) ferrocene, pyrrole was used in place of piperazine, and rubidium carbonate was used in place of t-butoxysodium. (Yield: 2'%).

$^1$H NMR (400 MHz, CDCl$_3$, TMS): δ=2.94 (s, 6H), 6,35 (t, J=2.2 Hz, 2H), 6.51 (d, J=3.6 Hz, 1H), 7.16 (t, J=2.2 Hz, 2H), 7.18 (dd, J=8.4 Hz, 1.8 Hz, 1H), 7.44 (d, J=3.8 Hz, 1H), 7.59 (d, J=8.1 Hz, 1H), 7.58 (d, J=1.8 Hz, 1H).

EXAMPLE 17

4-(1-pyrrolyl)-1-(dimethylamino)indole was prepared in the same manner as in Example 16 except that 2,6-dichlorophenylacetaldehyde N,N-dimethylhydrazone was used in place of 2,4-dichlorophenylacetaldehyde N,N-dimethylhydrazone. (Yield: 54%).

$^1$H NMR (400 MHz, CDC$_3$, TMS): δ=2.94 (s, 6H), 6.38 (t, J=2.2 Hz, 2H), 6,65 (d, J=3.3 Hz, 1H), 7.07 (d, J=7.3 Hz, 1H), 7.17 (t, J=2.2 Hz, 2H), 7.25 (t, J=7.3 Hz, 1H), 7.45 (d, J=3.3 Hz, 1H), 7.51 (d, J=7.3 Hz, 1H).

EXAMPLE 18

4-(1-indolyl)-1-(dimethylamino)indole was prepared in the same manner as in Example 16 except that 2,6-dichlorophenylacetaldehyde N,N-dimethylhydrazone was used in place of 2,4-dichlorophenylacetaldehyde N,N-dimethylhydrazone, and indole (212 mg, 1.81 mmol) was used in place of pyrrole. (Yield: 40%).

$^1$H NMR (400 MHz, CDCl$_3$, TMS): δ=2.96 (s, 6H), 6.36 (d, J=3.3 Hz, 1H), 6.71 (d, J=3.3 Hz, 1H), 7.12–7.19 (m, 2H), 7.21 (d, J=7.3 Hz, 1H), 7.32 (t, J=7.7 Hz, 1H), 7.42 (d, J=3.3 Hz, 1H), 7.43–7.46 (m, 1H), 7.48 (d, J=3.3 Hz, 1H), 7.60 (d, J=8.4 Hz, 1H), 7.68–7.73 (m, 1H).

Table 3 shows the source substances and the products in Examples 12–18.

TABLE 3

| Example No. | Source Substance | Product |
|---|---|---|
| 12 | 2,6-dichlorophenylacetaldehyde N,N-dimethylhydrazone | 4-(piperazin-1-yl)-1-(dimethylamino)indole |
| 13 | 2,6-dichlorophenylacetaldehyde N-methyl-N-phenylhydrazone | 4-(piperazin-1-yl)-1-(N-methyl-N-phenylamino)indole |
| 14 | 2,6-dichlorophenylacetaldehyde N,N-dimethylhydrazone | 4-(N-methyl-N-phenylamino)-1-(dimethylamino)indole |
| 15 | 2,4-dichlorophenylacetaldehyde N,N-dimethylhydrazone | 6-(piperazin-1-yl)-1-(dimethylamino)indole |

TABLE 3-continued

| Example No. | Source Substance | Product |
|---|---|---|
| 16 | | |
| 17 | | |
| 18 | | |

What is claimed is:

1. A nitrogen-heterocyclic compound represented by the Formula (I):

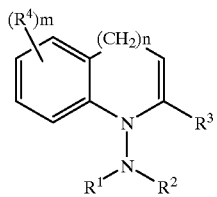

(1)

where $R^1$ and $R^2$ are independently hydrogen, an alkyl group, an aryl group selected from the group consisting of phenyl, 4-tolyl, 4-trifluoromethylphenyl, and 4-methoxyphenyl, or a heteroaryl group selected from the group consisting of 4-pyridyl, 3-pyridyl, 2-pyridyl, 2-furyl, and 2-thienyl; $R^3$ is hydrogen or an aryl group selected from the group consisting of phenyl, 4-tolyl, 4-trifluoromethylphenyl, 4-methoxyphenyl, and 4-biphenyl; $R^4$ is a substituted amino group selected from the group consisting of 1-piperazinyl, 4-methyl-1-piperazinyl, 3-methyl-1-piperazinyl, 1-homopiperazinyl, N-phenyl-N-methylamino, diphenylamino, di(p-tolyl)amino, N-(1-naphthyl)-N-phenylamino, N-(2-naphthyl)-N-phenylamino, N-(2-fluorenyl)-N-phenylamino, 1-pyrrolyl, 1-indolyl, and 9-carbazolyl, an alkoxy group, a nitro group, or halogen; m is an integer from 1 to 2; and n is 0 or 1.

2. A nitrogen-heterocyclic compound represented by Formula (2):

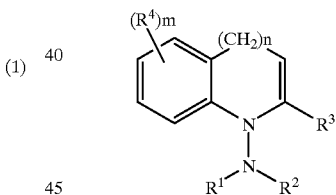

(2)

where $R^1$ and $R^2$ are independently hydrogen, an alkyl group, a phenyl group, a substituted phenyl group selected from the group consisting of 4-tolyl, 4-(t-butyl)phenyl, 4-fluorophenyl, 3-trifluoromethylphenyl, and 4-methoxyphenyl, a furyl group, or a thienyl group; $R^3$ is hydrogen or an aryl group selected from the group consisting of phenyl, 4-tolyl, 4-fluorophenyl, 3-trifluoromethylphenyl, 4-methoxyphenyl, and 4-biphenyl; $R^4$ is a substituted amino group selected from the group consisting of 1-piperazinyl, 4-methyl-piperazinyl, 3-methyl-1-piperazinyl, 1-homopiperazinyl, N-phenyl-N-methyl, diphenylamino, di(p-tolyl)amino, N-(1-naphthyl)-N-phenylamino, N-(2-naphthyl)-N-phenylamino, N-(2-fluorenyl)-N-phenylamino, 1-pyrrolyl, 1-indolyl, and 9-carbazolyl; m is 1 or 2; and n is 0 or 1.

3. The nitrogen-heterocyclic compound according to claim 2, wherein $R^1$ and $R^2$ in Formula (2) are independently an alkyl group.

4. The nitrogen-heterocyclic compound according to claim 2, wherein $R^1$ and $R^2$ in Formula (2) are independently a phenyl group or a substituted phenyl group selected from the group consisting of 4-tolyl, 4-(t-butyl)phenyl, 4-fluorophenyl, 3-trifluoromethylphenyl, and 4-methoxyphenyl.

5. The nitrogen-heterocyclic compound according to claim 2, 3 or 4, wherein m=1, and $R^4$ is at 4-position when n=0, and at 5-position when n=1 in Formula (2).

6. The nitrogen-heterocyclic compound according to claims 2, 3 or 4, wherein $R^4$ in Formula (2) is selected from 1-piperazinyl, 4-methyl-1-piperazinyl, 3-methyl-1-piperazinyl, 1-homopiperazinyl, N-phenyl-N-methylamino, diphenylamino, di(p-tolyl)amino, N-(1-naphthyl)-N-phenylamino, N-(2-naphthyl)-N-phenylamino, N-(2-fluorenyl)-N-phenylamino, 1-pyrrolyl, 1-indolyl, and 9-carbazolyl.

7. A nitrogen-heterocyclic compound according to claims 2, 3 or 4, wherein m is 1 in Formula (2).

8. A nitrogen-heterocyclic compound represented by Formula (3):

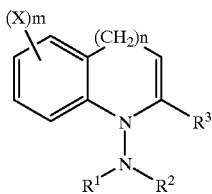

(3)

where $R^1$ and $R^2$ are independently a phenyl group or a substituted phenyl group selected from the group consisting of 4-tolyl, 4-(t-butyl)phenyl, 4-fluorophenyl, 3-trifluorometylphenyl, and 4-methoxyphenyl; a furyl group, or a thienyl group; R3 is hydrogen or an aryl group selected from the group consisting of phenyl, 4-tolyl, 4-fluorophenyl, 3-trifluoromethylphenyl, 4-methoxyphenyl, and 4-biphenyl; X is a halogen; m is 1 or 2; and n is 0 or 1.

9. A nitrogen-heterocyclic compound represented by Formula (3):

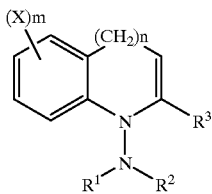

(3)

where $R^1$ and $R^2$ are independently an alkyl group; R3 is hydrogen or an aryl group selected from the group consisting of phenyl, 4-tolyl, 4-fluorophenyl, 3-trifluoromethylphenyl, 4-methoxyphenyl, and 4-biphenyl; X is a halogen: m is 1 or 2; and n is 0 or 1.

10. The nitrogen-heterocyclic compound according to claim 8 or 9, wherein m=1, and $R^4$ is at 4-position when n=0, and at 5-position when n=1 in Formula (3).

11. The nitrogen-heterocyclic compound according to claim 8 or 9 wherein m is 1 in Formula (3).

12. A process for producing the nitrogen-heterocyclic compound of claim 1, comprising cyclizing intramolecularly a hydrazone derivative represented by Formula (4) in the presence of a catalyst comprising a phosphine and a palladium compound, and a base:

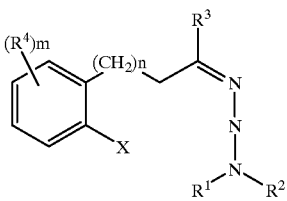

(4)

where $R^1$ and $R^2$ are independently hydrogen, an alkyl group, an aryl group selected from the group consisting of phenyl, 4-tolyl, 4-trifluoromethylphenyl, and 4-methoxyphenyl or a heteroaryl group selected from the group consisting of 4-pyridyl, 3-pyridyl, 2-pyridyl, 2-furyl, and 2-thienyl; $R^3$ is hydrogen or an aryl group selected from the group consisting of phenyl, 4-tolyl, 4-trifluoromethylphenyl, 4-methoxyphenyl, and 4-biphenyl; $R^4$ is a substituted amino group selected from the group consisting of 1-piperazinyl, 4-methyl-1piperazinyl, 3-methyl-1-piperazinyl, 1-homopiperazinyl, N-phenyl-N-methylamino, diphenylamino, di(p-tolyl)amino, N-(1-naphthyl)-N-phenylamino, N-(2-naphthyl)-N-phenylamino, N-(2-naphthyl)-N-phenylamino, N-(2-fluorenyl)-N-phenylamino, 1-pyrrolyl, 1-indolyl, and 9-carbazolyl, an alkoxy group, a nitro group, or halogen; X is a halogen; m is an integer from 0 to 2; and n is 0 or 1.

13. The process according to claim 12, wherein m=1, and $R^4$ is at 4-position when n=0, and at 5-position when n=1 in Formula (4).

14. The process according to claim 12 or 13, wherein the phosphine has a t-butyl-phosphorus linkage.

15. The process according to claim 12 or 13, wherein $R^4$ is a halogen.

16. The process according to claim 12 or 13, wherein m is 0 or 1.

17. A process for producing a nitrogen-heterocyclic compound of claim 2, comprising allowing a halogenated nitrogen-heterocyclic compound represented by Formula (3) to react with an amine in the presence of a catalyst comprising a phosphine and a palladium compound, and a base:

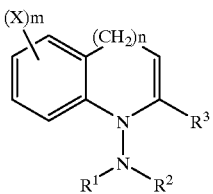

(3)

where $R^1$ and $R^2$ are independently hydrogen, an alkyl group, a phenyl group, a substituted phenyl group selected from the group consisting of 4-tolyl, 4(t-butyl)phenyl, 4-fluorophenyl, 3-trifluoromethylphenyl, and 4-methoxyphenyl, a furyl group, or a thienyl group; $R^3$ is hydrogen or an aryl group selected from the group consisting of phenyl, 4-tolyl, 4-fluorophenyl, 3-trifluoromethylphenyl, 4-methoxyphenyl, and 4-biphenyl; X is a halogen; m is 1 or 2; and n is 0 or 1.

18. The process according to claim 17, wherein the amine is selected from the group consisting of piperazine, 1-methylpiperazine, 2-methylpiperazine, homopiperazine, N-phenyl-N-methylamine, diphenylamine, di(p-tolyl)amine, N-(1-naphthyl)-N-phenylamine, N-(2-naphthyl)-N- phenylamine, N-(2-fluorenyl)-N-phenylamine, pyrrole, indole, and carbazole, and combination of two or more thereof.

19. A process for producing a substituted indole derivative represented by Formula (7):

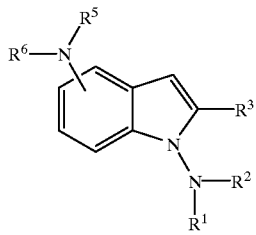

(7)

where $R^1$ and $R^2$ are independently hydrogen, an alkyl group, an aryl group selected from the group consisting of phenyl, 4-tolyl, 4-trifluoromethylphenyl, 4-methoxyphenyl, and 4-biphenyl, or a heteroaryl group selected from the group consisting of 4-pyridyl, 3-pyridyl, 2-pyridyl, 2-furyl, and 2-thienyl; $R^3$ is hydrogen or an aryl group selected from the group consisting of phenyl, 4-tolyl, 4-trifluoromehylphenyl, 4-methoxyphenyl, and 4-biphenyl; $R^5$ and $R^6$ are independently hydrogen, an alkyl group, or an aryl group, and $R^5$ and $R^6$ may be bonded to form a hetero-ring, said process comprising intramolecular cyclization of a compound represented by general formula (5):

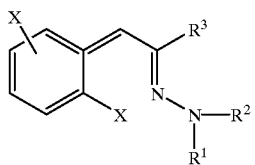

(5)

where $R^1$ and $R^2$ are independently hydrogen, an alkyl group, an aryl group selected from the group consisting of phenyl, 4-tolyl, 4-trifluoromethylphenyl, 4-methoxyphenyl, and 4-biphenyl, or a heteroaryl group selected from the group consisting of 4-pyridyl, 3-pyridyl, 2-pyridyl, 2-furyl, and 2-thienyl; $R^3$ is hydrogen or an aryl group selected from the group consisting of phenyl, 4-tolyl, 4-trifluoromethylphenyl, 4-methoxyphenyl, and 4-biphenyl; and X is a halogen, in the presence of a catalyst comprising a phosphine and a palladium compound, an amine represented by general formula (6).

$$R^5R^6NH$$

where $R^5$ and $R^6$ are independently hydrogen, an alkyl group, or an aryl group selected from the group consisting of phenyl, p-tolyl, p-methoxyphenyl, p-fluorophenyl, and m-(trifluoromethyl)phenyl, and $R^5$ and $R^6$ may be linked to form a hetero-ring selected from the group consisting of piperazine, 4-alkyl-1-piperazine, 3-methylpiperazine, homopiperazine, pyrrole, indole, and carbazole, and a base.

20. The process according to claim 19, wherein the phosphine has a t-butyl-phosphorus linkage.

* * * * *